(12) United States Patent  
Herrmann et al.

(10) Patent No.: US 8,079,100 B2  
(45) Date of Patent: Dec. 20, 2011

(54) APPARATUS FOR SUPPORTING A PATIENT FOR RADIATION THERAPY

(75) Inventors: Klaus Herrmann, Nürnberg (DE); Eike Rietzel, Darmstadt (DE); Andres Sommer, Langensendelbach (DE)

(73) Assignee: Siemens Aktiengesellschaft (DE)

( * ) Notice: Subject to any disclaimer, the term of this patent is extended or adjusted under 35 U.S.C. 154(b) by 748 days.

(21) Appl. No.: 11/991,752

(22) PCT Filed: Aug. 31, 2006

(86) PCT No.: PCT/EP2006/065851  
§ 371 (c)(1),  
(2), (4) Date: Mar. 10, 2008

(87) PCT Pub. No.: WO2007/033894  
PCT Pub. Date: Mar. 29, 2007

(65) Prior Publication Data  
US 2009/0122963 A1 May 14, 2009

(30) Foreign Application Priority Data

Sep. 19, 2005 (DE) .......................... 10 2005 044 651

(51) Int. Cl.  
*A61B 6/04* (2006.01)
(52) U.S. Cl. .............................. 5/601; 378/206; 378/209
(58) Field of Classification Search ...... 5/601; 378/206, 378/209  
See application file for complete search history.

(56) References Cited

U.S. PATENT DOCUMENTS

| 4,117,337 | A | * | 9/1978 | Staats .............................. 378/17 |
| 4,296,329 | A | * | 10/1981 | Mirabella .................. 250/491.1 |
| 4,481,657 | A | | 11/1984 | Larsson |
| 4,534,050 | A | * | 8/1985 | Smith ............................. 378/81 |
| 4,842,259 | A | | 6/1989 | Rice |
| 4,868,385 | A | | 9/1989 | Nishimura |
| 5,553,112 | A | | 9/1996 | Hardy et al. |
| 5,657,368 | A | | 8/1997 | Röckseisen |
| 5,697,164 | A | * | 12/1997 | Hausmann et al. ............. 33/512 |
| 6,078,036 | A | * | 6/2000 | Cook et al. .................. 250/206.1 |
| 6,094,760 | A | | 8/2000 | Nonaka et al. |
| 6,510,615 | B1 | | 1/2003 | Budd |
| 6,907,629 | B2 | * | 6/2005 | Longton et al. .................... 5/601 |
| 6,917,666 | B2 | * | 7/2005 | Wollenweber .................. 378/20 |
| 6,934,361 | B2 | * | 8/2005 | Ohkoda ........................ 378/98.8 |
| 7,147,371 | B2 | * | 12/2006 | Hecker .......................... 378/206 |
| 7,430,773 | B2 | * | 10/2008 | Brown et al. ...................... 5/601 |

FOREIGN PATENT DOCUMENTS

WO WO 03/039212 A 5/2003

OTHER PUBLICATIONS

The International Search Report dated Jan. 30, 2007, and translation of the PCT Written Opinion for International Application No. PCT/EP2006/065851.

* cited by examiner

*Primary Examiner* — Michael Trettel  
(74) *Attorney, Agent, or Firm* — Lempia Summerfield Katz LLC

(57) ABSTRACT

An apparatus for supporting a patient during radiation therapy includes a treatment table that is pivotable about a horizontal axis, and a laser measurement system which is designed to indicate a non-horizontal orientation of the treatment table to be adopted during the radiation therapy.

19 Claims, 4 Drawing Sheets

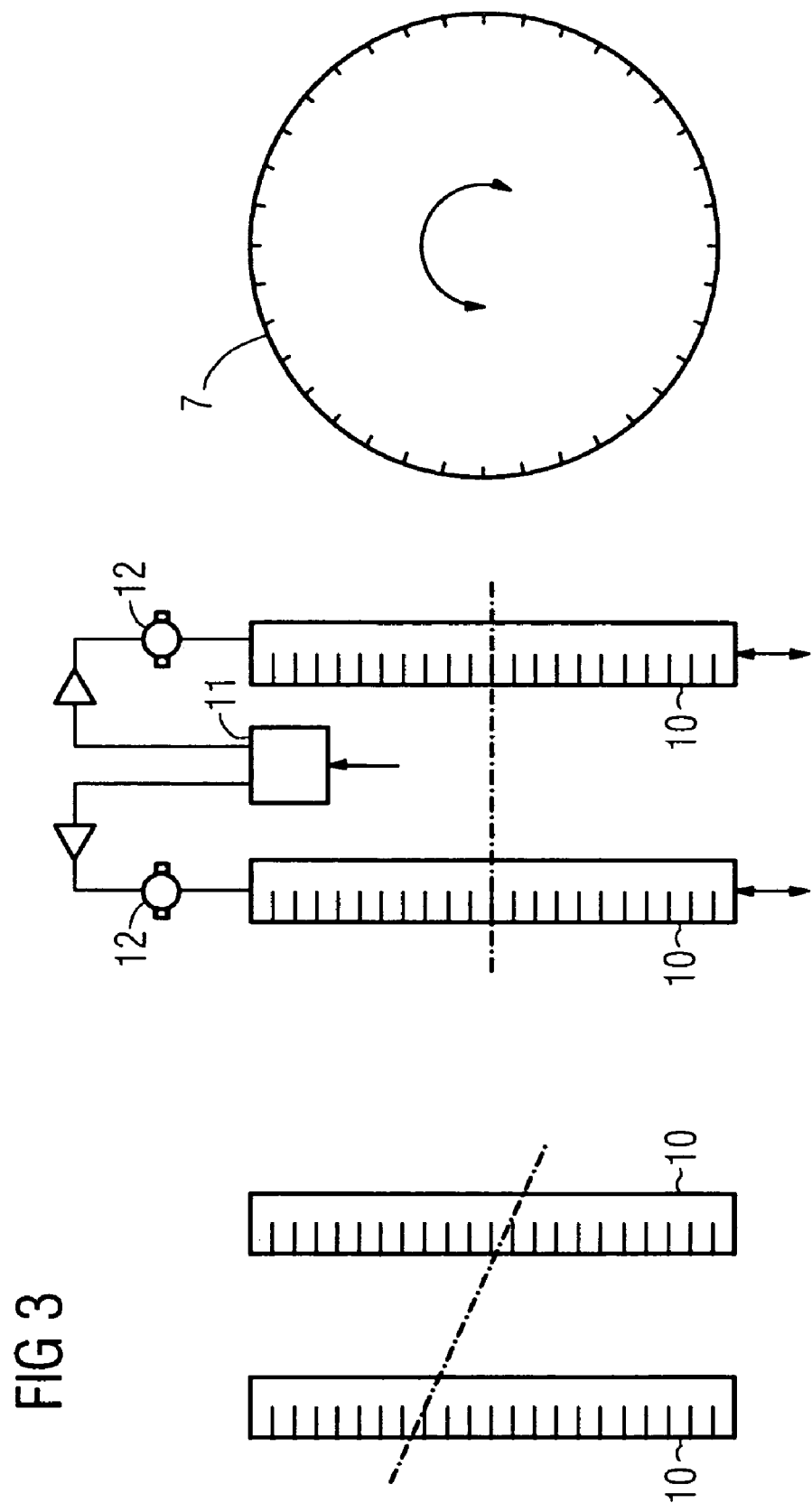

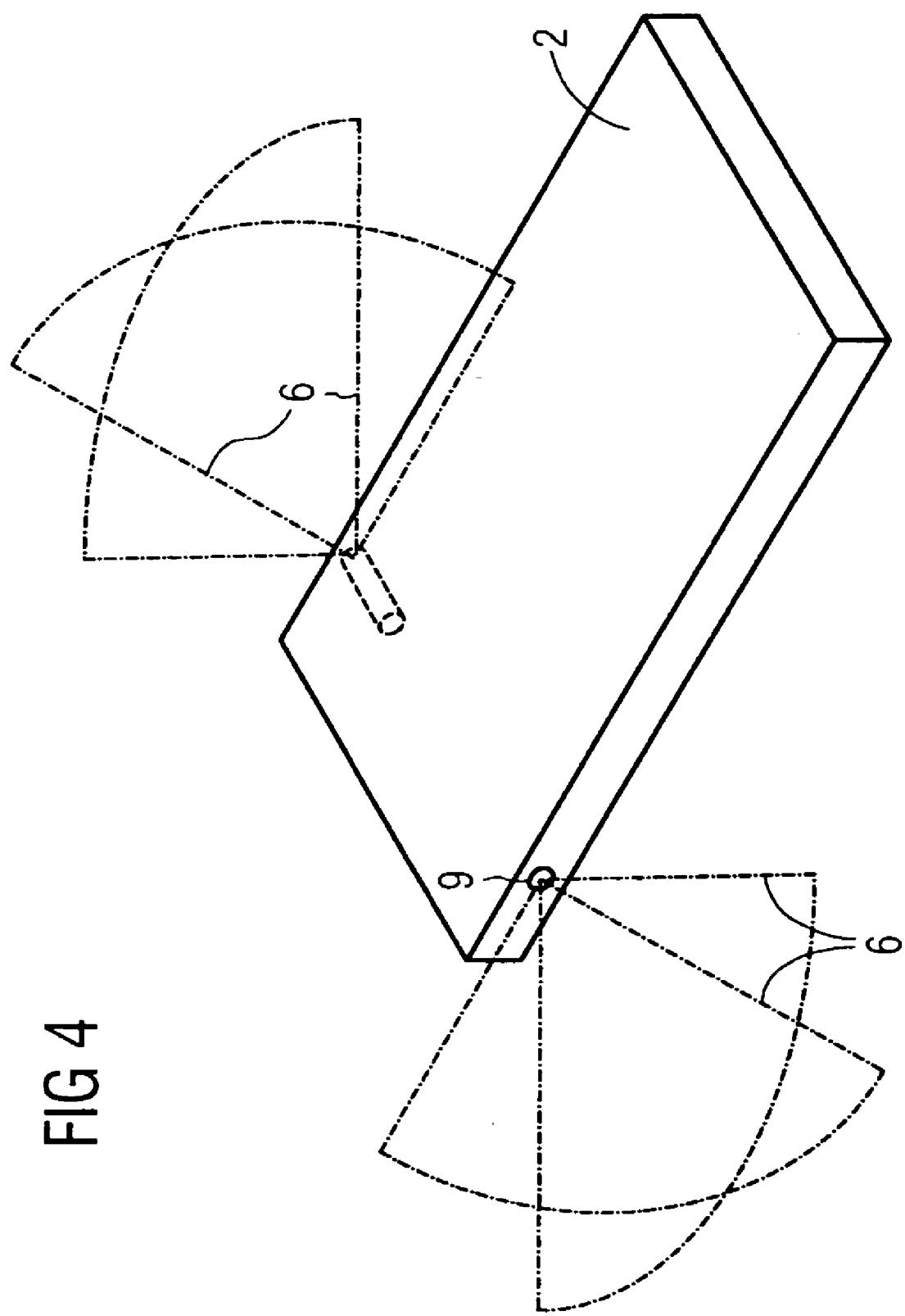

APPARATUS FOR SUPPORTING A PATIENT FOR RADIATION THERAPY

TECHNICAL FIELD

This application relates to an apparatus for supporting a patient for radiation therapy, in particular for use in a particle radiation treatment system.

BACKGROUND

An apparatus for supporting a patient in a radiation therapy system is known, for instance, from German Patent Disclosure DE 102 21 180 A1. The apparatus for supporting a patient includes a treatment table that is displaceable in a height-adjustable manner and can also be pivoted about more than one vertical axis. To level the treatment table exactly at the horizontal, a plurality of leveling devices, preferably three of them, are provided that have a wedge that is displaceable by a screw spindle or threaded spindle. The patient located on the leveled treatment table can be positioned, using a so-called laser cross, in such a way that the region to be irradiated is located at the isocenter of the radiation treatment system. The radiation treatment system has a gantry, with an emitter head that is pivotable about a horizontal axis.

SUMMARY AND DESCRIPTION

An apparatus for supporting a patient is disclosed. A treatment table is pivotable about at least one axis. The axis may be a horizontal axis and has at least one horizontal component. The treatment table may be pivotable about two horizontal axes that are perpendicular to one another. To position the treatment table in an inclined (non-horizontal) disposition, the apparatus for supporting a patient may have a laser measuring system. Because of the possibility of supporting a patient on a treatment table that is tilted in a defined way relative to the horizontal, the apparatus for supporting a patient is suitable for radiation therapy systems in which the radiation source or beam is not pivotable about a horizontal axis, or is pivotable to only a limited extent about a horizontal axis. In particular, the apparatus for supporting a patient is suitable for a radiation treatment system that operates with particle radiation.

The laser measuring system here may include one or more laser emitters as well as at least one display device, which may be in the form of a linear scale or a measuring disk. At least one laser emitter and at least one display device may be associated with each axis about which the treatment table can be pivoted. A beam cluster of the laser emitter illuminates the display means when the laser measuring system is in operation.

The display may be embodied such that because of the illuminating laser beam, a tilt angle of the treatment table relative to a horizontal axis can be determined from the display. The laser beam may be fan shaped.

In an aspect, the display is secured to a fixed structure, such as the wall of the treatment room or an immovable part of the radiation treatment system, while the laser emitter is fixedly connected to the treatment table. That display may be of a large size, and spaced apart from the treatment table by up to approximately several meters, facilitating the simple, exact setting of the angular position of the treatment table. The laser measuring system may include a plurality of optical radiation sources, whose radiation directions are orthogonal to one another. In a corresponding way, the planes in which linear scales or other display devices are disposed may also form a right angle with one another. In aspect, the laser measuring system may have a single optical radiation source that emits light which is directed in directions that may be orthogonal to one another.

In another aspect, a stereotactical frame may be secured to the treatment table and may support one or more optical radiation sources of the laser measuring system. The stereotactical frame has a fixed position relative to the patient's tissue to be irradiated. In the planning of the radiation treatment, the correct positioning of the stereotactical frame that can then be read off the display, is ascertained. In an alternative embodiment that may not have a stereotactical frame, the laser emitters (optical radiation sources) may be secured directly to the treatment table.

In another aspect, the display device of the laser measuring system is supported displaceably or pivotably. It is thus possible, before a radiation treatment is performed, for the measuring rod or measuring disk of the laser measuring system to be set in such a way that in the positioning of the treatment table, a defined marking on the display, which is may be identical in each radiation treatment, is illuminated by the laser emitter. In this way, the correct positioning of the patient may be simplified, and the risk of mis-positioning may be minimized.

In yet another aspect, the at least one display device is automatically adjustable. Using the planned positioning of the treatment table, in particular a tilt angle that the treatment table forms with the horizontal, the setting of the display device is calculated. The calculated setting value is transmitted to a control unit, which is connected to a drive unit that moves the display device to the desired position.

As an alternative to locating the laser emitter on the treatment table and the display device in the room, the display device is secured directly or indirectly to the treatment table, and the laser emitter is located off of the treatment table and independent of the motion of the treatment table. If the display device is secured indirectly, the display is located on the stereotactical frame. The laser emitter is located in a stationary fashion in the room.

Thus, by using an optical radiation source of a laser measuring system in cooperation with an automatically adjustable measuring rod or an automatically adjustable measuring disk, an inclined setting of the treatment table relative to a horizontal plane is determined.

BRIEF DESCRIPTION OF THE DRAWINGS

FIG. 3 shows a plurality of linear display devices and one display device in the form of a circular disk, as parts of laser measuring systems; and FIG. 4 is a perspective view of a treatment table with laser sources secured directly to the treatment table.

DESCRIPTION

Figure 1:
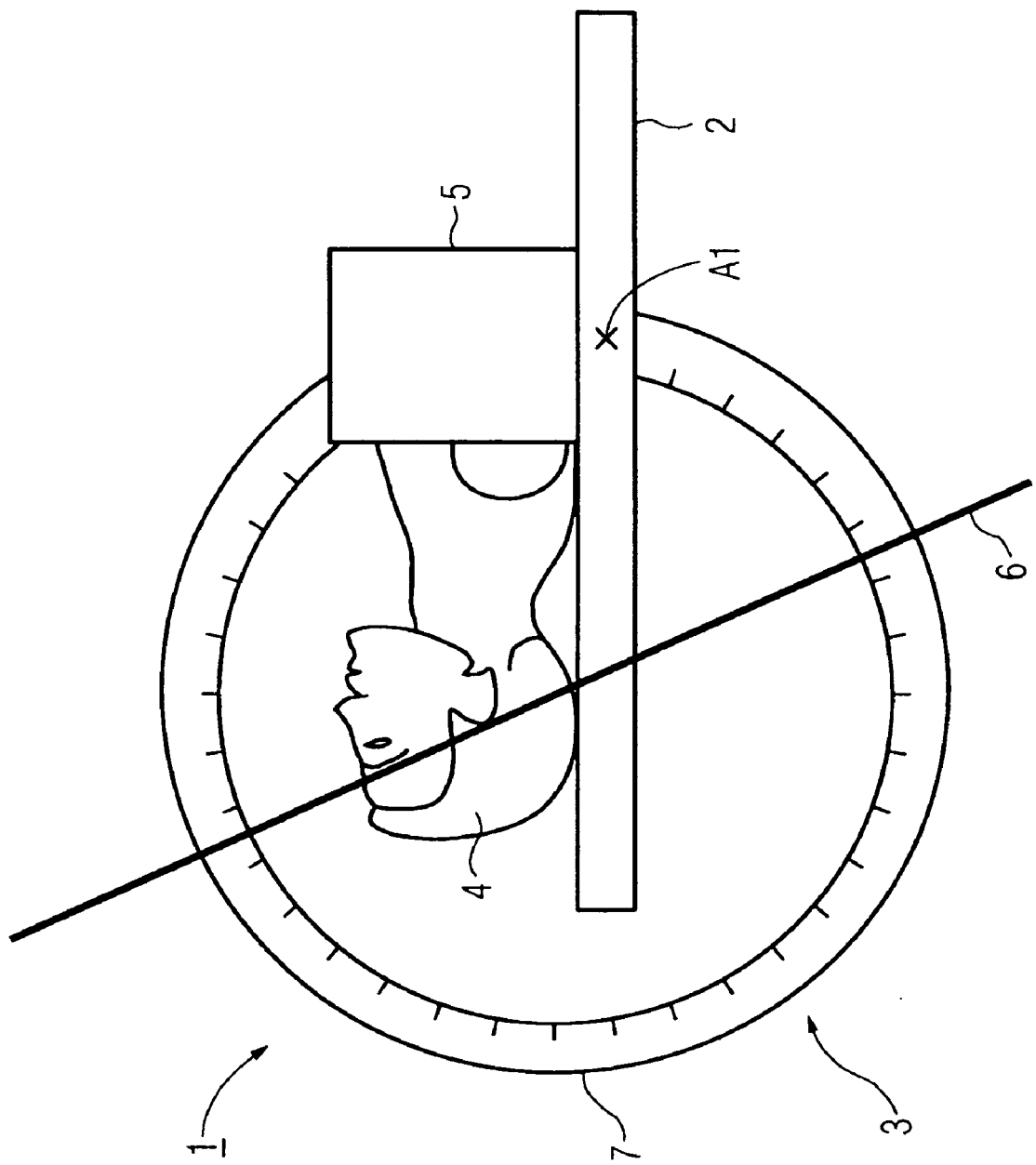
FIG. 1, in a schematic, fragmentary cross section, shows an apparatus for supporting a patient with a tiltable treatment table and with a laser measuring system.

FIG. 1 schematically shows an apparatus for supporting a patient 1. The apparatus includes both a treatment table 2 and a laser measuring system identified overall by reference numeral 3. The apparatus for supporting a patient 1 is part of a radiation treatment system, not further shown, with which a patient 4 is irradiated stereotactically. The treatment table 2 that supports the patient 4 is secured adjustably and tiltably about a horizontal axis A1, on a bracing structure 5.

A visible beam cluster 6 of the laser measuring system 3, in cooperation with a measuring disk 7, indicates the tilt angle of the treatment table 2; that is, the angle that the treatment table 2 forms with a horizontal plane. In FIG. 1, neither dimensions nor angles are shown to scale. The measuring disk 7, also known as a circular ruler, may serve as the display device of the laser measuring system 1. It may be secured, for example, to a rigid structure of the radiation treatment system. In a manner not visible from FIG. 1, the laser measuring system 3 includes a second measuring disk, which is located orthogonally to the measuring disk 7, and which indicates the tilting of the treatment table 2 about an axis that is orthogonal to the axis A1, and is likewise located in a horizontal plane. The measuring disks 7 may have a 360° graduation, but may also be subdivided in some other way.

Figure 2:
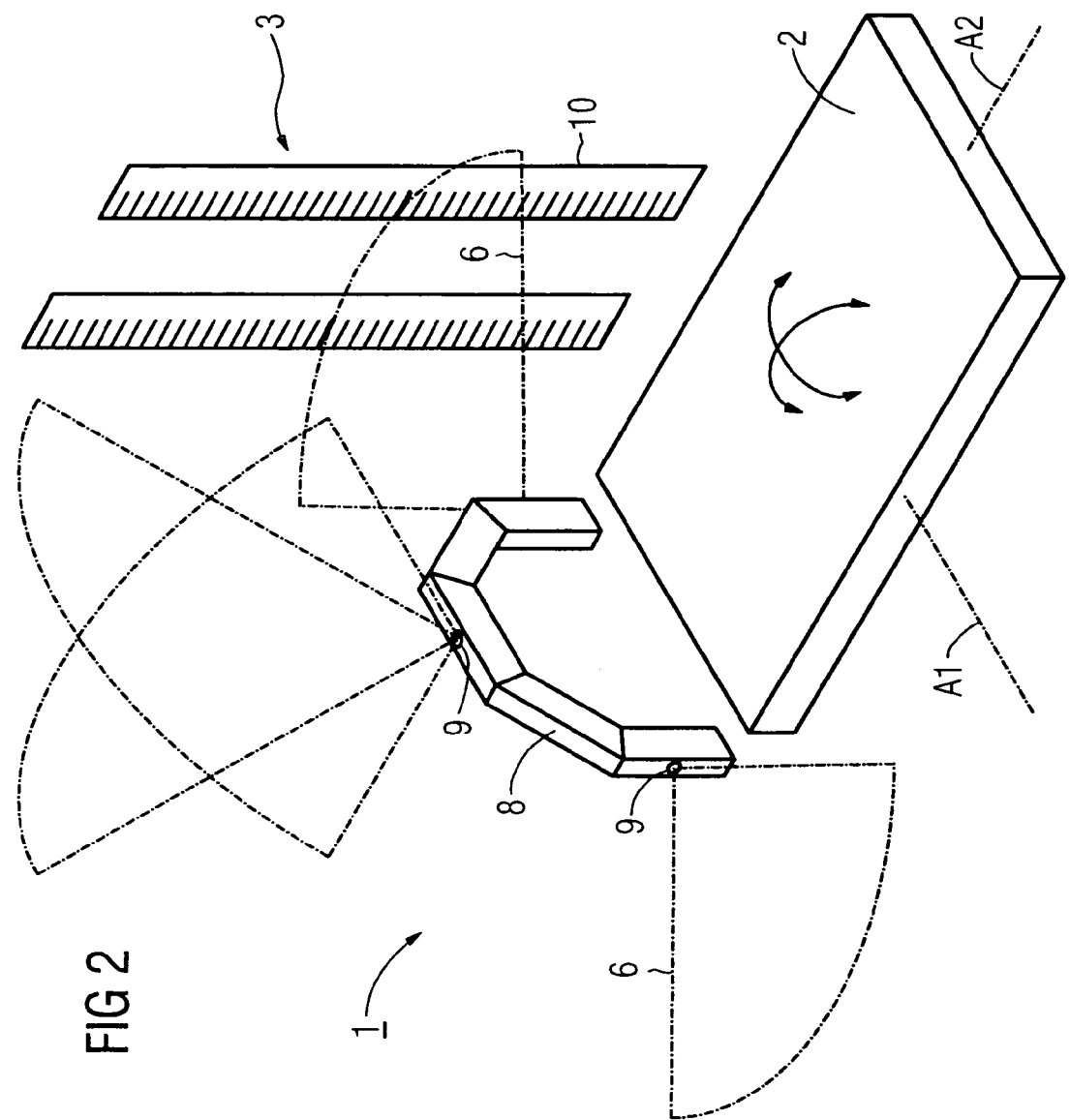
FIG. 2 is a perspective view of an apparatus for supporting a patient with a stereotactical frame secured to a treatment table.

The apparatus shown in FIG. 2 differs, amongst other ways, from the apparatus for supporting a patient 1 in FIG. 1 in that a stereotactical frame 8 is secured to the treatment table 2 and carries a plurality of laser emitters 9, whose beam clusters 6 define an orthogonal system. The treatment table 2 is tiltable both about an axis A1, and about a second axis A2 that is perpendicular to the first axis and is located in the longitudinal direction of the treatment table 2. The pivoting about the axis A2 is visualized using the two linear scales or measuring rods 10, which are mounted on the wall of the room in which the apparatus for supporting a patient 1 is disposed. Due to the large spacing distance of the linear scales 10 from the corresponding laser emitter 9, the laser measuring system 3 has high resolution. The measuring rods 10 simultaneously serve to indicate the positioning of the treatment table 2 in terms of height. In a manner not shown in the figure, another display is located on the ceiling of the room and is exposed to the laser emitter 9 located in a middle region of the stereotactical frame 8.

FIG. 3 shows examples of display devices 7, 10 that may be used with the laser measuring system 3. The two linear scales 10 on the left in the drawing are secured fixedly to a wall or other fixed construction. The illumination markings that are generated by the optical radiation of the laser emitter 9 are represented by a dot-dash line extending approximately diagonally. From the difference in height of the markings on the two measuring rods 10, a tilt angle of the treatment table 2 can be calculated.

In the linear scales 10, shown in the center of FIG. 3 provision is made for adjusting the height of the measuring rods 10 by a motor. For that purpose, a central control unit 11 may control two separate drive units 12: viz., one drive unit for each measuring rod 10. From a computation system that is used for controlling the radiation treatment, the set-point positioning of the treatment table 2 and, in particular, the tilt angle that is to be set, are transmitted to the control unit 11. Each measuring rod 10 is automatically set by the control unit 11 and the drive units 12 in such a way that the illumination of the fan beam or cluster beam 6 on both measuring rods having the same markings, such as the marking "±0", is brought into agreement.

Also shown in FIG. 3 is a measuring disk 7, which is pivotable about an axis located perpendicularly thereto. This pivoting motion is also, done automatically, similarly to the adjustment of the measuring rods 10. The beam cluster 6 emitted by a laser emitter 9 illuminates the measuring disk 7 with a linear marking. When the treatment table 2 has been tilted relative to the horizontal, this linear marking is correspondingly oblique. Prior to the radiation treatment, the control unit 11, not shown in this example, using a drive unit 12, such as a stepping motor, disposes the measuring disk 7 into a particular angular position. When the orientation of the treatment table 2 is correctly set, the illumination of the fan beam 6 strikes a defined marking, such as the "0°" marking, on the measuring disk 7.

FIG. 4 shows a treatment table 2, which differs from the embodiment of FIG. 2 primarily in that the laser emitters 9 are secured directly to the treatment table 2. In this example, adjustable display devices 7, 10 also cooperate with the laser emitters 9 to enable the tilt angles of the treatment table 2 to be set.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:

1. An apparatus for supporting a patient for radiation therapy, the apparatus comprising:
   a treatment table pivotable about an axis; and
   a laser measuring system including a display device, the laser measuring system being configured so as to permit a determination of a tilt angle of the treatment table relative to another axis,
   wherein the laser measuring system includes a laser emitter that is rigidly connected to the treatment table, and
   wherein a plurality of laser emitters which are oriented orthogonally to one another, are connected to the treatment table, the plurality of laser emitters comprising the laser emitter.

2. The apparatus of claim 1, wherein the display device is disposed so as to be illuminated by a laser beam emitted from the laser emitter.

3. The apparatus of claim 2, wherein the display device is disposed such that the tilt angle of the treatment table relative to the other axis is indicated on the display device by the laser beam.

4. The apparatus of claim 3, wherein the tilt angle is directly indicated on the display device.

5. The apparatus of claim 4, wherein the laser beam is a fan or cluster beam.

6. The apparatus of claim 1, wherein at least one of the axis and the other axis is a horizontal axis.

7. The apparatus of claim 1, wherein the treatment table is connected to a stereotactical frame.

8. The apparatus of claim 7, wherein at least one laser emitter of the plurality of laser emitters is disposed on the stereotactical frame.

9. The apparatus of claim 1, wherein the display device is a measuring rod.

10. The apparatus of claim 9, wherein the measuring rod is linearly positionable.

11. The apparatus of claim 1, wherein the display device is a measuring disk.

12. The apparatus of claim 11, wherein the measuring disk is pivotably supported.

13. The apparatus of claim 1, wherein the display device is automatically adjustable, and the adjustment of the display device is dependent on a desired set-point position of the treatment table.

14. The apparatus of claim 1, wherein the display device is mounted on the treatment table.

15. The apparatus of claim 1, wherein the axis is horizontal.

16. The apparatus of claim 1, wherein the axis is a first axis, and the other axis is a second axis,
  wherein the treatment table is pivotable about a third axis, and
  wherein a laser emitter of the plurality of laser emitters is associated with each of the first axis and the third axis about which the treatment table is pivotable.

17. The apparatus of claim 16, wherein a display device is associated with each of the first axis and the third axis about which the treatment table is pivotable.

18. An apparatus for supporting a patient for radiation therapy, the apparatus comprising:
  a treatment table pivotable about an axis; and
  a laser measuring system including a display device configured so as to permit determination of an orientation of the treatment table,
  wherein the laser measuring system includes a laser emitter that is rigidly connected to the treatment table, and
  wherein a plurality of laser emitters, which are oriented orthogonally to one another, are connected to the treatment table, the plurality of laser emitters comprising the laser emitter.

19. An apparatus for supporting a patient for radiation therapy, the apparatus comprising:
  a treatment table pivotable about an axis; and
  a laser measuring system including a display device configured so as to permit determination of an orientation of the treatment table,
  wherein the display device is a measuring disk, and
  wherein the measuring disk is pivotably supported.

* * * * *